(12) United States Patent
Suen et al.

(10) Patent No.: US 8,901,328 B2
(45) Date of Patent: Dec. 2, 2014

(54) METHOD FOR PREPARING MONO OR DIALKANOL AMIDES

(75) Inventors: Yat Fan Suen, Martinez, CA (US); Sarah Liz Jensen, Novato, CA (US)

(73) Assignee: Chervon Oronite Company LLC, San Ramon, CA (US)

( * ) Notice: Subject to any disclaimer, the term of this patent is extended or adjusted under 35 U.S.C. 154(b) by 287 days.

(21) Appl. No.: 13/444,007

(22) Filed: Apr. 11, 2012

(65) Prior Publication Data

US 2013/0274491 A1 Oct. 17, 2013

(51) Int. Cl.
*C07C 231/02* (2006.01)
*C07C 233/16* (2006.01)

(52) U.S. Cl.
CPC .............. *C07C 231/02* (2013.01); *C07C 233/16* (2013.01)
USPC ............. 554/66; 564/137; 564/133; 564/134; 564/135

(58) Field of Classification Search
None
See application file for complete search history.

(56) References Cited

U.S. PATENT DOCUMENTS

| | | | |
|---|---|---|---|
| 2,403,067 A | 7/1946 | Fischer et al. | |
| 2,863,888 A * | 12/1958 | Schurman | 554/66 |
| 3,040,075 A * | 6/1962 | Lohr | 554/66 |
| 3,257,436 A * | 6/1966 | Lindner | 554/69 |
| 4,293,432 A | 10/1981 | Papay et al. | |
| 4,389,322 A | 6/1983 | Horodysky | |
| 4,729,769 A | 3/1988 | Schlicht et al. | |
| 7,244,857 B2 | 7/2007 | Fox et al. | |
| 2006/0107584 A1 | 5/2006 | Simard et al. | |
| 2010/0010244 A1 | 1/2010 | Krull et al. | |

FOREIGN PATENT DOCUMENTS

WO 2009121485 10/2009

* cited by examiner

*Primary Examiner* — Yate K Cutliff

(57) ABSTRACT

Disclosed is a method involving reacting a deprotonated mono- or dialkanol amine with one or more $C_4$ to about $C_{75}$ fatty acid monoalcohol esters.

20 Claims, 2 Drawing Sheets

METHOD FOR PREPARING MONO OR DIALKANOL AMIDES

BACKGROUND OF THE INVENTION

1. Technical Field

The present invention generally relates to a method for preparing, mono or dialkanol amides.

2. Description of the Related Art

Engine oils typically use a mineral oil or a synthetic oil as a base oil. However, simple base oils alone do not provide the necessary properties to provide adequate friction reduction, wear protection, deposit control, etc. required to protect internal combustion engines. Thus, base oils are formulated with various additives (for imparting auxiliary functions) such as, for example, friction modifiers, ashless dispersants, metallic detergents (i.e., metal-containing detergents), antiwear agents, antioxidants (i.e., oxidation inhibitors), viscosity index improvers and the like to produce a compounded oil, i.e., a lubricating oil composition.

The petroleum industry has long recognized a need for greater fuel economy and efficiency in the operation of hydrocarbon fuel powered internal combustion engines, e.g., gasoline (i.e., spark-ignition) and diesel (i.e., compression-ignition) engines. For example, fuel economy standards mandated by the federal government have resulted in efforts by the automotive industry to improve the fuel economy of motor vehicles. One way to reduce fuel consumption is to reduce friction in particular areas of an internal combustion engine, e.g., bearings, valve trains, pistons, rings, water and oil pumps. By decreasing friction in these areas of the engine, improvement in fuel economy can also be achieved.

Accordingly, there has been a continual search for improved friction modifiers which decrease friction in strategic areas of the engine thereby improving the fuel economy of engine.

For example, U.S. Pat. No. 4,293,432 discloses a method of friction reduction in an internal combustion engine crankcase by using a formulated motor oil containing an ashless dispersant and about 0.1 to 1.5 weight percent of a reaction product of a fatty acid and monoethanolamine.

U.S. Pat. No. 4,389,322 ("the '322 patent") discloses the use of ethoxylated amides as friction modifiers in lubricants. The '322 patent further discloses that ethoxylated amides may be obtained from commercial sources or prepared by (1) the reaction of the appropriate hydrocarbyl amide with ethylene oxide, optionally in the presence of a catalyst, to form the corresponding ethoxylated amide or (2) the reaction of a hydrocarbyl carboxylic acid with an ethoxylated amine, e.g., bis(2-hydroxyethyl)oleamide formed by the reaction of oleic acid and diethanol amine.

U.S. Pat. No. 4,729,769 discloses a detergent additive for gasoline or lubricants, which contains the reaction product of a $C_6$ to $C_2O$ fatty acid ester such as coconut oil and a mono- or di-hydroxy hydrocarbyl amine such as diethanolamine.

U.S. Pat. No. 7,244,857 ("the '857 patent") discloses a method of making hydroxyalkyl amide composition with a decreased level of alkanolamine. The '857 patent further discloses that the method involves reacting at least one primary and/or secondary alkanolamine with at least one ester or fatty natural material, optionally in the presence of a catalyst such as an alkoxide or carbonate catalyst, to provide a reaction mixture containing hydroxyalkyl amide and unreacted alkanolamine, wherein the improvement comprises, carrying out the reaction of alkanolamine and ester in the presence of at least one metal silicate or treating the reaction mixture with at least one metal silicate.

U.S. Patent Application Publication No. 2010/0010244 discloses a method for producing fatty acid alkanol amides by first reacting at least one amine that contains at least one primary or secondary amino group and at least one hydroxyl group with at least one fatty acid to form an ammonium salt, and then converting the ammonium salt into the alkanol amide by way of microwave radiation.

Although the production of fatty acid alkanol amides as friction modifiers for fuel and lubricants has been quite extensive, most of the methods for their preparation produce a composition containing undesirable by-products along with the desired mono or dialkanol amide. In addition, the use of metal alkoxides such as potassium and sodium alkoxides as catalyst are expensive and can be neutralized by moisture or water resulting in possible handling issues, decrease in shelf life and even deactivation as a catalyst. In addition, if moisture is absorbed during the reaction, the metal alkoxide may be quenched thereby stopping the reaction. Accordingly, it would be advantageous to provide an improved method for producing mono or dialkanol amides that substantially avoids the formation of undesirable by-products.

SUMMARY OF THE INVENTION

In accordance with one embodiment of the present invention, there is provided a method comprising reacting a deprotonated mono- or dialkanol amine with one or more $C_4$ to about $C_{75}$ fatty acid monoalcohol esters.

In accordance with a second embodiment of the present invention, there is provided a method comprising (a) deprotonating a mono- or dialkanol amine with a deprotonating agent while continuously removing water formed from the reaction; and (b) reacting the deprotonated mono- or dialkanol amine with one or more $C_4$ to about $C_{75}$ fatty acid monoalcohol esters.

In accordance with a third embodiment of the present invention, there is provided a method comprising (a) deprotonating a mono- or dialkanol amine with an alkali metal hydroxide base while continuously removing water formed from the reaction; and (b) reacting the deprotonated mono- or dialkanol amine with one or more $C_4$ to about $C_{75}$ fatty acid monoalcohol esters.

Among, other factors, the: present invention is based on the discovery that by first deprotonating a mono- or dialkanol amine while continuously removing water formed from the reaction and then reacting the deprotonated mono- or dialkanol amine with one or more $C_4$ to about $C_{75}$ fatty acid monoalcohol esters, a mono or dialkanol amide can be formed with little to no by-product formations including ester amides and ester amines. Accordingly, mono or dialkanol amides can be prepared in a simple, cost efficient method.

DETAILED DESCRIPTION OF THE PREFERRED EMBODIMENTS

Figure 1:
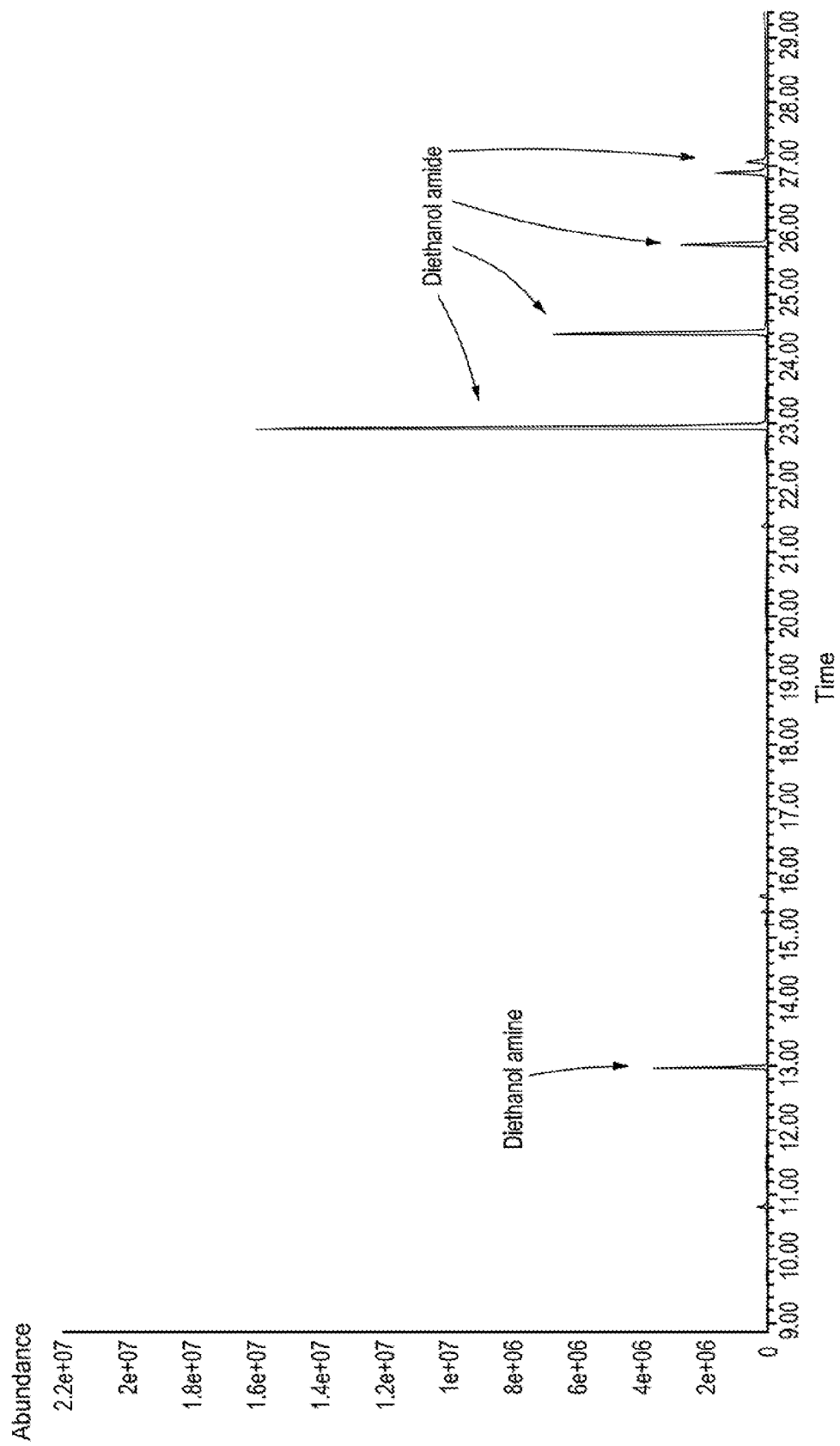
FIG. 1 is a GC/MS analysis of the reaction product obtained in Example 1.

The present invention is directed to a method for preparing mono or dialkanol amides. In one embodiment, the method involves reacting a deprotonated mono- or dialkanol amine with one or more $C_4$ to about $C_{75}$ fatty acid monoalcohol esters. In another embodiment, the method involves (a)

deprotonating a mono- or dialkanol amine with a deprotonating agent while continuously removing water formed from the reaction; and (b) reacting the deprotonated mono- or dialkanol amine with one or more $C_4$ to about $C_{75}$ fatty acid monoalcohol esters.

The mono- or dialkanol amine is first deprotonated with a suitable deprotonating agent while continuously removing water formed from the reaction to provide a deprotonated mono- or dialkanol amine. Generally, the mono- or dialkanol amine is a mono- or dialkanol amine with a primary or secondary amine nitrogen and at least one active hydrogen. In one embodiment, a mono- or dialkanol amine is represented by the formula:

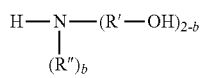

wherein R' is a divalent alkylene group having from 2 to about 10 carbon atoms, or from about 2 to 6, or from about 2 to 5 carbon atoms, or from about 2 to 3 carbon atoms, R" is hydrogen or an alkyl group having from 1 to 6 carbon atoms and "b" is 0 or 1.

Suitable mono- or dialkanol amines include, but are not limited to, ethanolamine, propanolamine, isopropanolamine, butanolamine, isobutanolamine, methylethanolamine, butylethanolamine, diethanolamine, dipropanolamine, diisopropanolamine, dibutanolamine, diisobutanolamine, and the like and mixtures thereof.

Suitable deprotonating agents include any deprotonating agent capable of deprotonating the mono- or di-hydroxyalkyl amine. In general, useful deprotonating agents are strong bases such as hydroxide bases, e.g., potassium hydroxide, barium hydroxide, cesium hydroxide, sodium hydroxide, strontium hydroxide, calcium hydroxide, rubidium hydroxide, lithium hydroxide, $Sr(OH)_2$, $Mg(OH)_2$, and combinations thereof, lithium bases, e.g., lithium dialkylamide, an aryl lithium, an arylalkyl lithium and an alkyl lithium such as a $C_1$ to about $C_{10}$ alkyl lithium, and the like and mixtures thereof. Examples of lithium bases include methyl lithium, butyl lithium (BuLi) such as n-BuLi, sec-BuLi, and t-BuLi, hexyl lithium, heptyl lithium, octyl lithium, phenyl lithium, and the like and mixtures thereof.

Deprotonation can be effected by heating a mixture of the mono- or dialkanol amine and the deprotonation agent to a temperature and time period sufficient to deprotonate the mono- or dialkanol amine while continuously removing water produced during the reaction. By the end of the reaction, little to no water is present and a deprotonated mono- or dialkanol amine is obtained. Reaction may typically be effected by maintaining the reactants at a temperature of from about 30° C. to about 300° C., or from about 100° C. to about 150° C. for about 0.5 to about 5 hours. In addition, the reaction is ordinarily carried out under vacuum and under a nitrogen purge. The reaction can be solventless or carried out in a solvent, preferably one which is compatible with the ultimate composition in which the product is to be used.

Generally, the molar ratio of mono- or dialkanol amine to deprotonating agent will ordinarily range from about 0.1:1 to about 100:1.

Next, the deprotonated mono- or dialkanol amine is reacted with one or more $C_4$ to about $C_{75}$ fatty acid monoalcohol esters to provide the resulting mono- or dialkanol amide. In general, a $C_4$ to about $C_{75}$ fatty acid monoalcohol ester is a reaction product of one or more fatty acids with one or more monoalcohols. The fatty acid monoalcohol esters can contain from about $C_4$ to about $C_{75}$ fatty acid monoalcohol esters or from about $C_6$ to about $C_{24}$ fatty acid monoalcohol esters or from about $C_8$ to about $C_{22}$ fatty acid monoalcohol esters. As one skilled in the art will readily appreciate, the about $C_4$ to about $C_{75}$ fatty acid monoalcohol esters can be the same or different fatty acid monoalcohol esters. Fatty acids are a class of compounds containing a long hydrocarbon chain and a terminal carboxylate group and are characterized as unsaturated or saturated depending upon whether a double bond is present in the hydrocarbon chain. Therefore, an unsaturated fatty acid has at least one double bond in its hydrocarbon chain whereas a saturated fatty acid has no double bonds in its fatty acid chain. Preferably, the acid is saturated.

In one embodiment, a fatty acid used to make the fatty acid monoalcohol esters is derived from natural sources such as, for example, beef tallow oil, lard oil, palm oil, castor oil, cottonseed oil, corn oil, peanut oil, soybean oil, sunflower oil, olive oil, whale oil, menhaden oil, sardine oil, coconut oil, palm kernel oil, babassu oil, rape oil, soya oil and the like and mixtures thereof.

In one embodiment, a fatty acid used to make the fatty acid monoalcohol esters is an unsaturated fatty acid including, by way of example, myristoleic acid, palmitoleic acid, oleic acid, linolenic acid, and the like and mixtures thereof. In one embodiment, a fatty acid used to make the fatty acid monoalcohol ester is a saturated fatty acid including, by way of example, include caproic acid, caprylic acid, capric acid, lauric acid, myristic acid, palmitic acid, stearic acid, arachidic acid, behenic acid, lignoceric acid, and the like and mixtures thereof.

In one embodiment, a fatty acid used to make the fatty acid monoalcohol esters can vary depending on the desired fatty acid ester, but can include butyric, caproic, caprylic, capric, decenoic, lauric, cis-9-dodecenoic, myristic, myristoleic, cis-9-tetradecenoic, pentadecanoic, palmitic, palmitoleic, cis-9-hexadecenoic, heptadecanoic, heptadecenoic, stearic, oleic, linoleic, linolenic, ricinoleic, dihydroxystearic, nonadecanoic, arachidic, cis-9, cis-11-eicosenoic, eicosadienoic, eicosatrienoic, arachidonic, eicosapentaenoic, behenic, erucic, docosadienoic, 4,8,12,15,19-docosapentaenoic, docosahexaenoic, lignoceric, tetracosenoic and the like and mixtures thereof.

Suitable monoalcohols used to make the fatty acid monoalcohol esters include $C_1$ to $C_{20}$ linear or branched monoalcohols or $C_1$ to $C_{12}$ linear or branched monoalcohols. Examples of such monoalcohols include, but are not limited to, methanol, ethanol, propanol, propan-2-ol, isopropanol, butanol, sec-butanol, tert-butanol, 2-ethyl-hexanol, and the like.

In one embodiment, the ester will be a fatty acid methyl ester or mixture of fatty acid methyl esters, e.g., where the fatty acid of the ester is a fatty acid derived from coconut oil and the monoalcohol of the ester is methanol, although any monoalcohol ester or mixtures thereof of the above-described materials can be used, e.g., where the fatty acid of the ester is a fatty acid derived from coconut oil and the monoalcohol of the ester is one or more of methanol, ethanol, propanol, etc.

The $C_4$ to about $C_{75}$ fatty acid monoalcohol esters used in the method of the present invention can be obtained by methods known in the art or are commercially available from such sources as, for example, Cognis Corporation under the tradename Agnique, e.g. Agnique ME 12-18-U.

Reaction of the one or more $C_4$ to about $C_{75}$ fatty acid monoalcohol esters and deprotonated mono- or dialkanol amine may be effected by heating the ester and deprotonated mono- or dialkanol amine to a suitable temperature to produce the desired product. The reaction may typically be effected by maintaining the reactants at a temperature of from about 30° C. to about 150° C., or from about 50° C. to about 120° C. for about 0.5 to about 8 hours. Generally, the amount of deprotonated mono- or dialkanol amine and ester will be in a molar ratio of deprotonated mono- or dialkanol amine to ester of from about 0.1:1 to about 10:1 or from about 0.8:1 to about 1.3:1.

The reaction can be solventless or carried out in a solvent, preferably one which is compatible with the ultimate composition in which the product is to be used.

Particularly useful solvents include at least aromatic solvents such as, for example, Aromatic-100, Aromatic-150, Shellsolv AB, Avjet, toluene, xylene, and mixtures thereof. The method of the present invention is conducted without glycerin.

The method of the present invention advantageously provides mono- or dialkanol amides with little to no by-product formations including ester amides and ester amines. Generally, previously known methods for preparing alkanol amides would typically form a reaction product which was a, complex mixture of compounds including at least fatty amides; fatty acid esters, fatty acid ester-amides, unreacted starting reactants, free fatty acids, glycerol, and partial fatty acid esters of glycerol (i.e., mono- and di-glycerides). For example, a representation of the various amounts of the various compounds constituting the complex mixture of the reaction product is as follows: about 5 to about 65 mole % of fatty amide, about 3 to about 30 mole % fatty acid ester, about 5 to about 65 mole % fatty acid ester-amide, about 0.1 to about 50 mole % partial fatty acid ester, about 0.1 to about 30 mole % glycerol, about 0.1 to about 30 mole % free fatty acids, about 0.1 to about 30 mole % charge alkanolamine, about 0.1 to about 30 mole % charge glycerides, etc. However, the method of the present invention will form the resulting mono or dialkanonol amides in relatively pure form, i.e., containing relatively little to no by-products.

The resulting mono or dialkanonol amides obtained in the method of the present invention is of the following structure:

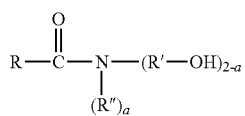

wherein R is a hydrocarbyl group having from about 3 to about 75, or from about 6 to about 24, or from about 8 to about 22, carbon atoms; R' is a divalent alkylene group having from 2 to about 10, or from about 2 to 6, or from about 2 to 5, or from about 2 to 3, carbon atoms; R" is hydrogen or an alkyl group having from 1 to 6 carbon atoms and a is 0 or 1. In one embodiment, a is 0.

Examples of the mono- or dialkanol amide moiety of the resulting mono- or dialkanol amides obtained in the method of the present invention include, but are not limited to, ethanol amide, diethanol amide, propanol amide, dipropanol amide, and the like and mixtures thereof.

In one embodiment, the acid moiety of the resulting mono- or dialkanol amides may be RCO— wherein R is an alkyl or alkenyl hydrocarbon group containing from about 3 to about 19 carbon atoms typified by caprylic, caproic, capric, lauric, myristic, palmitic, stearic, oleic, linoleic, etc. In one embodiment, the acid is saturated although unsaturated acid may be present.

In one embodiment, the reactant bearing the acid moiety may be derived from a natural oil: coconut, babassu, palm kernel, palm, olive, castor, peanut, rape, beef tallow, lard, lard oil, whale blubber, sunflower, etc.

The resulting mono- or dialkanol amide produced by the method of the invention can be used to provide a decrease in friction in an internal combustion engine, e.g., a spark-ignition engine or compression-ignition engine, through its use as a fuel or lubricant additive. In one embodiment, the resulting mono- or dialkanol amide produced by the methods of the invention will be employed in a friction-modifying or lubricity effective amount in a fuel composition containing a major amount of a liquid hydrocarbon fuel. The fuel can be any internal combustion engine hydrocarbon fuel, e.g., diesel, gasoline, jet fuels, etc.; alcoholic fuels such as methanol or ethanol; or a mixture of any of the foregoing.

When the fuel is diesel, such fuel generally boils above about 212° F. The diesel fuel can comprise atmospheric distillate or vacuum distillate, or a blend in any proportion of straight run and thermally and/or catalytically cracked distillates. Preferred diesel fuels have a cetane number of at least 40, preferably above 45, and more preferably above 50. The diesel fuel can have such cetane numbers prior to the addition of any cetane improver. The cetane number of the fuel can be raised by the addition of a cetane improver.

When the fuel is gasoline, it can be derived from straight-chain naphtha, polymer gasoline, natural gasoline, catalytically cracked or thermally cracked hydrocarbons, catalytically reformed stocks, etc. It will be understood by one skilled in the art that gasoline fuels typically boil in the range of about 80° to 450° F. and can contain straight chain or branched chain paraffins, cycloparaffins, olefins, aromatic hydrocarbons, and any mixture of these.

Generally, the composition of the fuel is not critical and any conventional motor fuel base can be employed in the practice of this invention.

The proper concentration of the resulting mono- or dialkanol amide produced by the methods of the invention that is necessary to achieve the desired friction modification in the fuel composition is dependent upon a variety of factors including, for example, the type of fuel used, the presence of other additives, etc. Generally, however, the range of the resulting mono- or dialkanol amide concentration in the fuel composition is from about 10 to about 10,000 parts per million and preferably from about 30 to about 5000 parts per million of the additive per part of base fuel. If other friction modifiers are present, a lesser amount of the resulting mono- or dialkanol amide additive may be used.

The resulting mono- or dialkanol amide additive described herein may also be formulated as a fuel concentrate, using an inert stable oleophilic organic solvent boiling in the range of about 150° F. to about 400° F. In one embodiment, a suitable inert stable oleophilic organic solvent includes aliphatic or an aromatic hydrocarbon solvents, e.g., solvents such as benzene, toluene, xylene or higher-boiling aromatics or aromatic thinners. Aliphatic alcohols of about 3 to 8 carbon atoms, e.g., isopropanol, isobutylcarbinol, n-butanol and the like, in combination with hydrocarbon solvents are also suitable for use with the fuel additive. In the fuel concentrate, the amount of the additive will be ordinarily be about 5 or more wt. % and generally not exceed about 70 wt. %, preferably from about 5 wt. % to about 50 wt. % and more preferably from about 10 wt. % to about 25 wt. %.

In another embodiment, the resulting mono- or dialkanol amide produced by the method of the invention will be employed in a friction-modifying or lubricity effective amount in a lubricating oil composition containing a major amount of an oil of lubricating viscosity, also referred to as a base oil. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered oil of lubricating viscosity used in formulating a lubricating oil composition for any and all such applications.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used herein will have a kinematic viscosity range at 100° C. of about 5.5 cSt to about 10 cSt. In one embodiment, the base oils used herein will have a kinematic viscosity range at 100° C. of about 4 cSt to about 12 cSt. The base oil will be selected or blended depending on the desired end use and the additives in the finished oil to give the desired grade of oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30, 15W-40, 30, 40 and the like. In general, the oil of lubricating viscosity can be either synthetic or natural mineral oil based fluids categorized by API as Group I, Group II, Group II, Group IV or Group V base oils or combinations thereof.

The proper concentration of the resulting mono- or dialkanol amide produced by the method of the invention that is necessary to achieve the desired friction modification in the lubricating oil composition is dependent upon a variety of factors including, for example, the type of oil of lubricating viscosity used, the presence of other additives, etc. Generally, however, the range of the resulting mono- or dialkanol amide concentration in the lubricating oil composition is from about 0.1 to about 20 wt. %, based on the total weight of the lubricating oil composition. If other friction modifiers are present, a lesser amount of the resulting mono- or dialkanol amide additive may be used.

The resulting mono- or dialkanol amide additive described herein may also be formulated as a lubricating oil concentrate, using a substantially inert, normally liquid organic diluent such as, for example, mineral oil, naphtha, benzene, toluene or xylene to form an additive concentrate. These concentrates usually contain from about 20% to about 80% by weight of such diluent. Typically a neutral oil having a viscosity of about 4 to about 8.5 cSt at 100° C. and preferably about 4 to about 6 cSt at 100° C. will be used as the diluent, though synthetic oils, as well as other organic liquids which are compatible with the additive and finished lubricating oil can also be used. The additive package can contain one or more other various additives, referred to below, in the desired amounts and ratios to facilitate direct combination with the requisite amount of the major amount of an oil of lubricating viscosity.

The lubricating oil compositions may also contain conventional lubricating oil composition additives for imparting auxiliary functions to give a finished lubricating oil composition in which these additives are dispersed or dissolved. For example, the lubricating oil compositions can be blended with friction modifiers other than the resulting fatty acid alkanol amide additive described herein, antioxidants, ashless dispersants, anti-wear agents, detergents such as metal detergents, rust inhibitors, dehazing agents, demulsifying agents, metal deactivating agents, pour point depressants, antifoaming agents, co-solvents, package compatibilisers, corrosion-inhibitors, dyes, extreme pressure agents and the like and mixtures thereof. A variety of the additives are known and commercially available. These additives, or their analogous compounds, can be employed for the preparation of the lubricating oil compositions of the invention by the usual blending procedures.

Each of the foregoing additives, when used, is used at a functionally effective amount to impart the desired properties to the lubricant. Thus, for example, if an additive is an ashless dispersant, a functionally effective amount of this ashless dispersant would be an amount sufficient to impart the desired dispersancy characteristics to the lubricant. Generally, the concentration of each of these additives, when used, may range, unless otherwise specified, from about 0.001% to about 20% by weight, and in one embodiment about 0.01% to about 10% by weight based on the total weight of the lubricating oil composition.

The following non-limiting examples are illustrative of the present invention.

EXAMPLE 1

Preparation of Diethanol Cocamide.

Diethanolamine (22.1 grams (g)) and potassium hydroxide (0.05 eq, 0.6 g) were charged into a round bottom reaction flask; under a house vacuum and nitrogen purge. The reactants were mixed for 1 hour at 110° C. to continuously remove the water produced by this reaction. Next, the temperature was lowered to 60° C. and coconut oil methyl ester (50.0 g) from Cognis Corporation (Agnique ME 12-18-U) was charged with a dropping funnel over a period of 30 to 45 minutes. The reaction was held at 60° C. for 2.5 hours.

COMPARATIVE EXAMPLE A

Preparation of a coconut oil-diethanol amine reaction product according to step 1a of Example 1 of U.S. Patent Application Publication No. 20060107584.

To a flask equipped with a mechanical stirrer and thermometer was added 2000 g of coconut oil methyl ester with less than 0.05 wt. % glycerol. Then 926 g of diethanolamine was added. The mixture was heated to about 150° C. for about 4 hours. At the end of the reaction time, the mixture is cooled to about 95° C. and stripped under vacuum at about 450 mm Hg to remove methanol.

GC-MS

Figure 2:
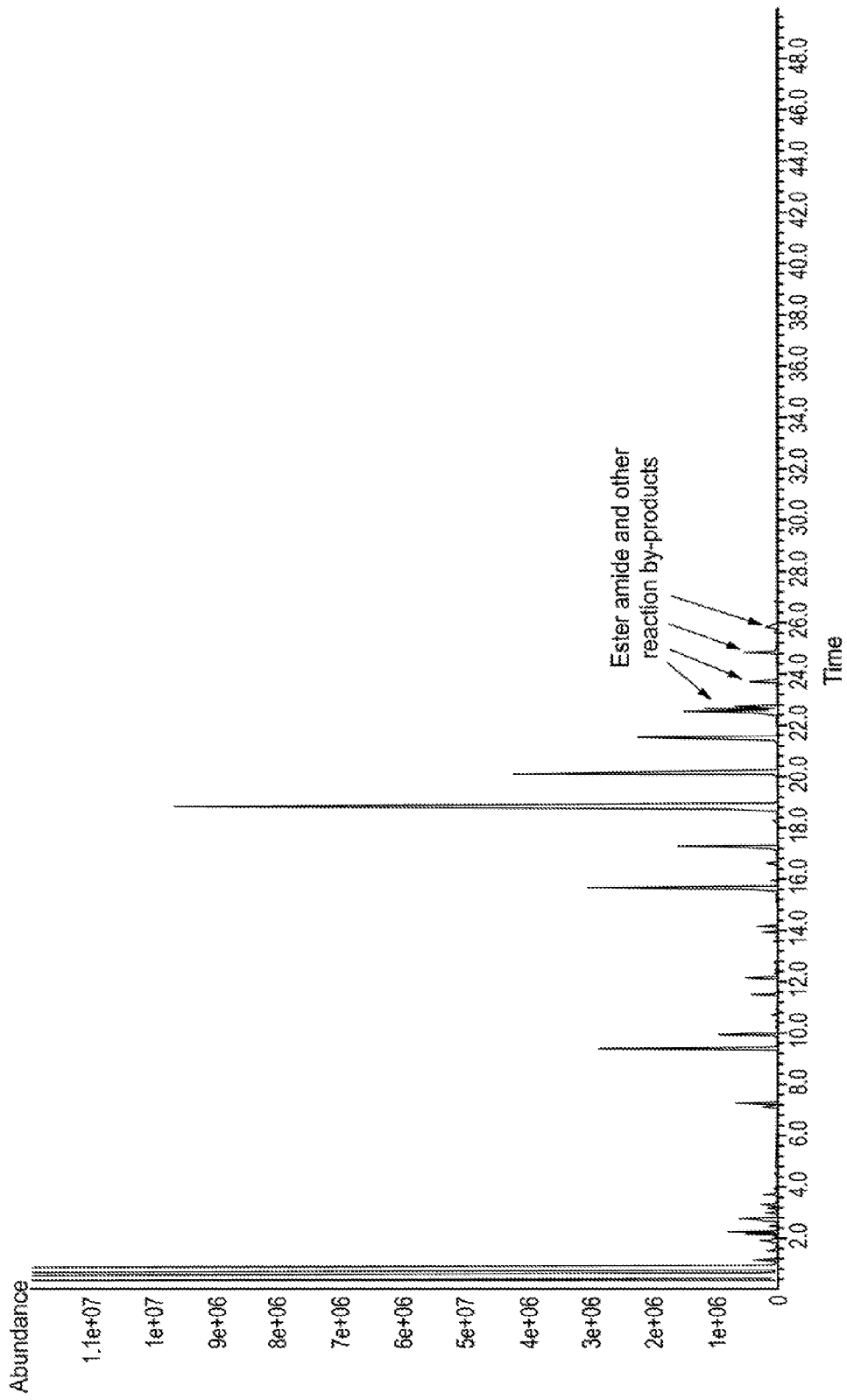
FIG. 2 is a GC/MS analysis of the reaction product obtained in Comparative Example A.

The resulting products of Example 1 and Comparative Example A were analyzed by gas chromatography-mass spectrometry to verify their purity. For the product of Example 1, the GC-MS analysis according to FIG. 1 showed diethanol amide as the primary product. However, no other side products were found by GC-MS analysis. For the product of Comparative Example A, the GC-MS analysis according to FIG. 2 showed that it contained the desired amide products as well as a number of by products such as ester amide, ester amine and the like.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method comprising reacting a deprotonated mono- or dialkanol amine with one or more $C_4$ to about $C_{75}$ fatty acid monoalcohol esters.

2. The method of claim 1, wherein the mono- or dialkanol amine of the deprotonated mono- or dialkanol amine is of the general formula:

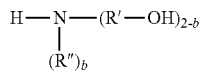

wherein R' is a divalent alkylene group having from 2 to about 10 carbon atoms, R" is hydrogen or an alkyl group having from 1 to 6 carbon atoms and b is 0 or 1.

3. The method of claim 1, wherein the mono- or dialkanol amine of the deprotonated mono- or dialkanol amine is selected from the group consisting of ethanolamine, propanolamine, isopropanolamine, butanolamine, isobutanolamine, methylethanolamine, butylethanolamine, diethanolamine, dipropanolamine, di isopropanolamine, dibutanolamine, diisobutanolamine, and combinations thereof.

4. The method of claim 1, wherein the one or more $C_4$ to about $C_{75}$ fatty acid monoalcohol esters are a fitly acid methyl ester, fatty acid ethyl ester, fatty acid propyl ester, fatty acid butyl ester or mixtures thereof.

5. The method of claim 1, wherein the fatty acid of the fatty acid monoalcohol ester is a fatty acid derived from beef tallow oil, lard oil, palm oil, castor oil, cottonseed oil, corn oil, peanut oil, soybean oil, sunflower oil, olive oil, whale oil, menhaden oil, sardine oil, coconut oil, palm kernel oil, babassu oil, rape oil, soya oil or mixtures thereof.

6. The method of claim 1. wherein the fatty acid of the ester is a fatty acid derived from coconut oil and the monoalcohol of the ester is selected from the group consisting of methanol, ethanol, propanol, propan-2-ol, isopropanol, butanol, sec-butanol, tert-butanol and 2-ethyl-hexanol.

7. The method of claim 1, wherein the deprotonated mono- or dialkanol amine is obtained by deprotonating a mono- or dialkanol amine with a deprotonating agent while continuously removing water formed from the deprotonation reaction.

8. The method of claim 7, wherein the mono- or dialkanol amine possesses the general formula:

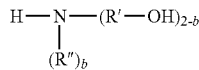

wherein R' is a divalent alkylene group having from 2 to about 10 carbon atoms, R" is hydrogen or an alkyl group having from 1 to 6 carbon atoms and b is 0 or 1.

9. The method of claim 7, wherein the mono- or dialkanol amine is selected from the, group consisting of ethanolamine, propanolamine, isopropanolamine, butanolamine, isobutanolamine, methylethanolamine, butylethanolamine, diethanolamine, dipropanolamine, diisopropanolamine, dibutanolamine, diisobutanolamine, and combinations thereof.

10. The method of claim 7, wherein the deprotonating agent is a strong base.

11. The method of claim 7, wherein the deprotonating agent is a hydroxide base.

12. The method of claim 11, wherein the hydroxide base is potassium hydroxide or sodium hydroxide.

13. The method of claim 7, wherein the mono- or dialkanol amine is reacted with the deprotonating agent in a molar ratio of mono- or dialkanol amine to deprotonating agent of about 0.1:1 to about 100:1.

14. The method of claim 7, wherein the mono- or dialkanol amine is diethanol amine and the ester is a fatty acid methyl ester.

15. The method of claim 7, wherein the fatty acid of the fatty acid monoalcohol ester is a fatty acid derived from beef tallow oil, lard oil, palm oil, castor oil, cottonseed oil, corn oil, peanut oil, soybean oil, sunflower oil, olive oil, whale oil, menhaden oil, sardine oil, coconut oil, palm kernel oil, babassu oil, rape oil, soya oil or mixtures thereof.

16. The method of claim 7, wherein the mono- or dialkanol amine is selected from the group consisting, of monoethanolamine, diethanolamine, propanolamine, isopropanolamine, dipropanolamine, di-isopropanolamine, butanolamine, aminoethylaminoethanol and combinations thereof and the fatty acid of the fatty acid ester is a fatty acid derived from beef tallow oil, lard oil, palm oil, castor oil, cottonseed oil, corn oil, peanut oil, soybean oil, sunflower oil, olive oil, whale oil, menhaden oil, sardine oil, coconut oil, palm kernel oil, babassu oil, rape oil, soya oil or mixtures thereof.

17. The method of claim 1, wherein the deprotonated mono- or dialkanol amine is reacted with the ester in a molar ratio of deprotonated mono- or dialkanol amine to ester of about 0.1:1 to about 10:1.

18. The method of claim 7, wherein the mono- or dialkanol amine is reacted with the deprotonating agent at a temperature of about 30 to about 300° C.

19. The method of claim 1 wherein the deprotonated mono or dialknol amine is reacted with the ester at a temperature of about 30 to about 150° C.

20. The method of claim 1, wherein a reaction product of the deprotonated mono- or dialkanol amine with one or more $C_4$ to about $C_{75}$ fatty acid monoalchohol esters is substantially free of any by-products.

* * * * *

UNITED STATES PATENT AND TRADEMARK OFFICE
CERTIFICATE OF CORRECTION

| | | |
|---|---|---|
| PATENT NO. | : 8,901,328 B2 | Page 1 of 1 |
| APPLICATION NO. | : 13/444007 | |
| DATED | : December 2, 2014 | |
| INVENTOR(S) | : Suen et al. | |

It is certified that error appears in the above-identified patent and that said Letters Patent is hereby corrected as shown below:

ON THE TITLE PAGE

Page 1, change "Sarah Liz Jensen" to -- Sarah Elizabeth Jensen --.

Signed and Sealed this
Fifteenth Day of December, 2015

Michelle K. Lee
*Director of the United States Patent and Trademark Office*